(12) United States Patent
Fukui et al.

(10) Patent No.: US 9,138,492 B2
(45) Date of Patent: Sep. 22, 2015

(54) PARTICLE CONTAINING HYDROPHOBIC DYE HAVING CYANINE STRUCTURE, AND CONTRAST AGENT CONTAINING THE PARTICLE

(71) Applicant: CANON KABUSHIKI KAISHA, Tokyo (JP)

(72) Inventors: Tatsuki Fukui, Yokohama (JP); Fumiko Tomatsu, Yokohama (JP); Kengo Kanazaki, Kyoto (JP); Satoshi Yuasa, Yokohama (JP); Mayuko Kishi, Machida (JP); Daisuke Sasaguri, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/770,536

(22) Filed: Feb. 19, 2013

(65) Prior Publication Data

US 2013/0224121 A1 Aug. 29, 2013

(30) Foreign Application Priority Data

Feb. 23, 2012 (JP) ................................ 2012-038035

(51) Int. Cl.
  *A61K 49/22* (2006.01)
  *A61K 49/00* (2006.01)

(52) U.S. Cl.
  CPC ........... *A61K 49/225* (2013.01); *A61K 49/0032* (2013.01); *A61K 49/0093* (2013.01)

(58) Field of Classification Search
  CPC . A61K 49/22; A61K 49/225; A61K 49/0093; A61K 49/0036
  USPC ........ 424/1.11, 1.65, 1.69, 1.73, 9.1, 9.3–9.8; 514/2, 359, 430
  See application file for complete search history.

(56) References Cited

U.S. PATENT DOCUMENTS

| | | |
|---|---|---|
| 6,190,641 B1 | 2/2001 | Achilefu et al. |
| 6,264,919 B1 | 7/2001 | Achilefu et al. |
| 6,424,857 B1 | 7/2002 | Henrichs et al. |
| 6,498,945 B1 | 12/2002 | Alfheim et al. |
| 7,767,194 B2 * | 8/2010 | Achilefu et al. ............... 424/9.1 |
| 2002/0022004 A1 | 2/2002 | Licha et al. |
| 2008/0181965 A1 | 7/2008 | Leon et al. |
| 2010/0034748 A1 | 2/2010 | Li et al. |
| 2012/0052011 A1 | 3/2012 | Fukui et al. |
| 2012/0052017 A1 | 3/2012 | Kato et al. |
| 2012/0070375 A1 | 3/2012 | Tabata et al. |
| 2013/0209368 A1 * | 8/2013 | Magdassi et al. ............... 424/9.6 |

FOREIGN PATENT DOCUMENTS

WO   WO-91/05545   *   5/1991

OTHER PUBLICATIONS

Isabella Texier et al. Cyanine-Loaded lipid nanoparticles for improved in vivo fluorescence imaging, Journal of Biomedical Optics, 14(5), 054005-1054005-11, 2009.*
Qun-Li et al. Synthesis and Characterization of Heptamethine Cyanine Dyes, Molecules, 1997, 2, 91-98.*
Bruce A. Kerwin, Polysorbate 20 and 80 Used in the Formulation of Protein Biotherapeutics: Structure and Degradation Pathways, Journal of Pharmaceutical Sciences, vol. 97(8), 2924-2935, 2008.*
Vishal Saxena et al., "Enhanced Photo-Stability, Thermal-Stability and Aqueous-Stability of Indocyanine Green in Polymeric Nanoparticulate Systems," 74 J. Photochem. Photobiol. B: Biology 29-38 (2004).
Yvonne Kohl et al., "Preparation and Biological Evaluation of Multifunctional PLGA-Nanoparticles Designed for Photoacoustic Imaging," 7(2) Nanomedicine 228-237 (Apr. 2011).
J. Gravier et al., "Lipid Nanoparticles (LNP): a New Technology for Fluorescence Contrast Agents with Improved Properties," 7576 Proc. SPIE 75761H-1-75761H-10 (2010).

\* cited by examiner

*Primary Examiner* — Michael G Hartley
*Assistant Examiner* — Jagadishwar Samala
(74) *Attorney, Agent, or Firm* — Fitzpatrick, Cella, Harper & Scinto (57) ABSTRACT

Provided is a particle which can stably hold a dye in itself even in an aqueous solution such as serum, in order to solve such a problem of a particle containing ICG, which has been conventionally used in a contrast agent or the like, that the ICG is a dye having a hydrophilic functional group and hence the ICG leaks out of the particle in an aqueous solution such as serum. More specifically, provided is a particle including a hydrophobic dye having a cyanine structure, in which the hydrophobic dye is represented by the following chemical formula (1).

Chemical formula (1)

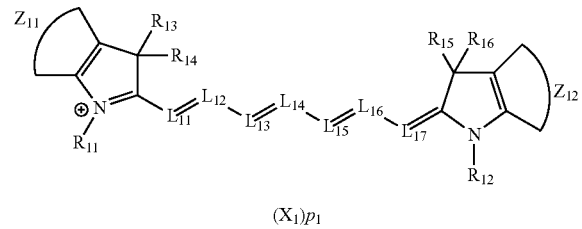

6 Claims, 1 Drawing Sheet

PARTICLE CONTAINING HYDROPHOBIC DYE HAVING CYANINE STRUCTURE, AND CONTRAST AGENT CONTAINING THE PARTICLE

BACKGROUND OF THE INVENTION

1. Field of the Invention

The present invention relates to a particle containing a hydrophobic dye having a cyanine structure, and to a contrast agent containing the particle.

2. Description of the Related Art

In recent years, a fluorescence imaging method or a photoacoustic imaging method has attracted attention as an imaging method which allows non-invasive diagnosis.

In the fluorescence imaging method, a fluorescent dye is irradiated with light and fluorescence thus emitted from the dye is detected. It is widely used in various types of imaging. In the photoacoustic imaging method, a molecule as an object to be measured is irradiated with light to allow a heat release due to volume expansion of a molecule of the irradiated object, and an intensity and generation position of an acoustic wave resulting from the volume expansion is detected, to thereby obtain an image of the object to be measured. In the fluorescence imaging method or photoacoustic imaging method, a dye may be used as a contrast agent for increasing an intensity of fluorescence or an acoustic wave from a site to be measured.

Indocyanine green (hereinafter may be abbreviated as ICG) is known as a dye to emit an acoustic wave due to light absorption. It should be noted that the ICG as used herein refers to a compound having a cyanine structure and having a structure shown below.

In this regard, however, $H^+$ or $K^+$ as well as $Na^+$ may be used as a counter ion.

In this connection, Journal of Photochemistry and Photobiology B: Biology, 74 (2004) 29-38 (hereinafter, abbreviated as Non Patent Literature 1) discloses an ICG-containing poly (lactide-co-glycolide) acid (hereinafter may be abbreviated as PLGA) particle obtained by an emulsion solvent diffusion method using polyvinyl alcohol (PVA) as a surfactant.

The ICG-containing particle disclosed in Non Patent Literature 1 involves a problem in that, since the ICG is a dye having a hydrophilic functional group, in an aqueous solution such as serum, the ICG may leak out of the particle.

SUMMARY OF THE INVENTION

In view of the foregoing, an object of the present invention is to provide a particle which can, through use of a hydrophobic dye having a cyanine structure, stably hold a dye in itself even in an aqueous solution such as serum.

A first aspect of the present invention relates to a particle, including: a hydrophobic dye having a cyanine structure; and a surfactant, in which the hydrophobic dye is represented by the following chemical formula (1).

A second aspect of the present invention relates to a particle, including: a hydrophobic dye having a cyanine structure; and a matrix material encapsulating the hydrophobic dye, in which the hydrophobic dye is represented by the following chemical formula (1):

Chemical formula (1)

$(X_1)p_1$ where: $L_{11}$, $L_{12}$, $L_{13}$, $L_{14}$, $L_{15}$, $L_{16}$, and $L_{17}$ may be identical to or different from one another and each represent CH or $CR_{17}$; $R_{17}$ represents a functional group selected from the group consisting of a halogen atom, an acetoxy group, an amino group, a nitro group, a cyano group, and an alkyl group having 1 to 18 carbon atoms, or $R_{17}$ may form a four-membered ring to a six-membered ring together with an alkyl group bonded to another $L_{11}$, $L_{12}$, $L_{13}$, $L_{14}$, $L_{15}$, $L_{16}$, or $L_{17}$; $R_{11}$, $R_{12}$, $R_{13}$, $R_{14}$, $R_{15}$, and $R_{16}$ may be identical to or different from one another and each represent a hydrogen atom, a halogen atom, an acetoxy group, an amino group, a nitro group, a cyano group, or an alkyl group having 1 to carbon atoms or aromatic group substituted or unsubstituted by one or more functional groups selected from a halogen atom, an acetoxy group, an amino group, a nitro group, a cyano group, and an alkyl group having 1 to carbon atoms; $Z_{11}$ and $Z_{12}$ may be identical to or different from each other and each represent a structure required for bonding to a five-membered heterocyclic ring to form a five-membered or six-membered condensed ring, provided that the condensed ring may further have one or more substituents selected from a halogen atom, an acetoxy group, an amino group, a nitro group, a cyano group, and an alkyl group having 1 to 18 carbon atoms, or a condensed ring; $X_1$ represents a counter ion required for neutralizing a charge of a molecule; and $p_1$ represents the number of $X_1$'s required for neutralizing a charge of an entire molecule.

According to the present invention, there can be provided a particle which can, through use of a hydrophobic dye having a cyanine structure, stably hold a dye in itself even in an aqueous solution such as serum.

Further features of the present invention will become apparent from the following description of exemplary embodiments with reference to the attached drawings.

DESCRIPTION OF THE EMBODIMENTS

Hereinafter, embodiments of the present invention are described. However, the present invention is by no means limited thereto. First, contents common to first and second embodiments are described.

(Hydrophobic Dye Having Cyanine Structure)

In the present invention, the term "dye" is defined as a compound that can absorb light having a wavelength of from 600 nm to 1,300 nm.

Further, in this embodiment, the term "hydrophobic dye" is defined as a dye having an Rf value of 0.09 or more and 0.50 or less, which is calculated by a thin-layer liquid chromatography (hereinafter may be abbreviated as TLC) method to be described later in Examples.

In this embodiment, the structure of a hydrophobic dye having a cyanine structure is represented by the following chemical formula (1):

Chemical formula (1)

where: $L_{11}, L_{12}, L_{13}, L_{14}, L_{15}, L_{16}$, and $L_{17}$ may be identical to or different from one another and each represent CH or $CR_{17}$; $R_{17}$ represents a functional group selected from the group consisting of a halogen atom, an acetoxy group, an amino group, a nitro group, a cyano group, and an alkyl group having 1 to 18 carbon atoms, or $R_{17}$ may form a four-membered ring to a six-membered ring together with an alkyl group bonded to another $L_{11}, L_{12}, L_{13}, L_{14}, L_{15}, L_{16}$, or $L_{17}$ such as a methylene group, a dimethylene group, or a trimethylene group; $R_{11}, R_{12}, R_{13}, R_{14}, R_{15}$, and $R_{16}$ may be identical to or different from one another and each represent a hydrogen atom, a halogen atom, an acetoxy group, an amino group, a nitro group, a cyano group, or an alkyl group having 1 to 18 carbon atoms or aromatic group substituted or unsubstituted by one or more functional groups selected from a halogen atom, an acetoxy group, an amino group, a nitro group, a cyano group, and an alkyl group having 1 to 18 carbon atoms; $Z_{11}$ and $Z_{12}$ may be identical to or different from each other and each represent a structure required for bonding to a five-membered heterocyclic ring to form a five-membered or six-membered condensed ring, provided that the condensed ring may further have one or more substituents selected from a halogen atom, an acetoxy group, an amino group, a nitro group, a cyano group, and an alkyl group having 1 to 18 carbon atoms, or a condensed ring; $X_1$ represents a counter ion required for neutralizing a charge of a molecule; and $p_1$ represents the number of $X_1$'s required for neutralizing a charge of an entire molecule.

The hydrophobic dye according to this embodiment may have a structure represented by the following chemical formula (2).

Chemical formula (2)

(In the formula: $L_{21}, L_{22}, L_{23}, L_{24}, L_{25}, L_{26}$, and $L_{27}$ may be identical to or different from one another and each represent CH or $CR_{27}$; $R_{27}$ represents a functional group selected from the group consisting of a halogen atom, an acetoxy group, an amino group, a nitro group, a cyano group, and an alkyl group having 1 to 18 carbon atoms; $R_{27}$ may form a four-membered ring to a six-membered ring together with an alkyl group bonded to another $L_{21}, L_{22}, L_{23}, L_{24}, L_{25}, L_{26}$, or $L_{27}$; $X_2$ represents a counter ion required for neutralizing a charge of a molecule; $p_2$ represents the number of $X_2$'s required for neutralizing a charge of an entire molecule; $A_{21}$ represents any one of structures represented by the following chemical formula (3) and chemical formula (4); and $A_{22}$ represents any one of structures represented by the following chemical formula (5) and chemical formula (6).)

Chemical formula (3)

$R_{31}, R_{33}, R_{34}, R_{301}, R_{302}, R_{303}$, and $R_{304}$ may be identical to or different from one another and each represent a hydrogen atom, a halogen atom, an acetoxy group, an amino group, a nitro group, a cyano group, or an alkyl group having 1 to 18 carbon atoms or aromatic group substituted or unsubstituted by one or more functional groups selected from a halogen atom, an acetoxy group, an amino group, a nitro group, a cyano group, and an alkyl group having 1 to 18 carbon atoms.

A dotted line represents a bonding portion to $L_{21}$.

Chemical formula (4)

$R_{41}, R_{43}, R_{44}, R_{401}, R_{402}, R_{403}, R_{404}, R_{405}$, and $R_{406}$ may be identical to or different from one another and each represent a hydrogen atom, a halogen atom, an acetoxy group, an amino group, a nitro group, a cyano group, or an alkyl group having 1 to 18 carbon atoms or aromatic group substituted or unsubstituted by one or more functional groups selected from a halogen atom, an acetoxy group, an amino group, a nitro group, a cyano group, and an alkyl group having 1 to 18 carbon atoms.

A dotted line represents a bonding portion to $L_{21}$.

Chemical formula (5)

$R_{52}$, $R_{55}$, $R_{56}$, $R_{501}$, $R_{502}$, $R_{503}$, and $R_{504}$ may be identical to or different from one another and each represent a hydrogen atom, a halogen atom, an acetoxy group, an amino group, a nitro group, a cyano group, or an alkyl group having 1 to 18 carbon atoms or aromatic group substituted or unsubstituted by one or functional groups selected from a halogen atom, an acetoxy group, an amino group, a nitro group, a cyano group, and an alkyl group having 1 to 18 carbon atoms.

A dotted line represents a bonding portion to $L_{27}$.

Chemical formula (6)

$R_{62}$, $R_{65}$, $R_{66}$, $R_{601}$, $R_{602}$, $R_{603}$, $R_{604}$, $R_{605}$, and $R_{606}$ may be identical to or different from one another and each represent a hydrogen atom, a halogen atom, an acetoxy group, an amino group, a nitro group, a cyano group, or an alkyl group having 1 to 18 carbon atoms or aromatic group substituted or unsubstituted by one or more functional groups selected from a halogen atom, an acetoxy group, an amino group, a nitro group, a cyano group, and an alkyl group having 1 to 18 carbon atoms.

A dotted line represents a bonding portion to $L_{27}$.

Since the hydrophobic dye according to this embodiment has a conjugated double bond, it can absorb light having a specific wavelength. Thus, the hydrophobic dye can be used for photoacoustic imaging or fluorescence imaging.

The hydrophobic dye according to this embodiment may have a molar absorption coefficient of $10^6$ $M^{-1}$ $cm^{-1}$ or more at at least one wavelength selected from the range of 600 nm to 1,300 nm.

Examples of the hydrophobic dye having a cyanine structure may include 1,1',3,3,3',3'-hexamethylindotricarbocyanine iodide <chemical formula (A1)>, 3H-indolium, 1-ethyl-2-[7-(1-ethyl-1,3-dihydro-3,3-dimethyl-2H-indol-2-ylidene)-1,3,5-heptatrien-1-yl]-3,3-dimethyl-, iodide <chemical formula (A2)>, 2-[2-[2-chloro-3-[2-(1,3-dihydro-1,1,3-trimethyl-2H-benzo[e]-indol-2-ylidene)-ethylidene]-1-cyclohexen-1-yl]-ethenyl]-1,1,3-trimethyl-1H-benzo[e] indolium perchlorate <chemical formula (A3)>, 1,1',3,3,3', 3'-hexamethylindotricarbocyanine perchlorate <chemical formula (C1)>, and 1,1',3,3,3',3'-hexamethyl-4,4',5,5'-dibenzo-2,2'-indotricarbocyanine perchlorate <chemical formula (C2)>.

Chemical formula (A1)

Chemical formula (A2)

Chemical formula (A3)

Chemical formula (C1)

Chemical formula (C2)

(Surfactant)

A particle according to first embodiment contains a surfactant. A surface of a particle according to second embodiment may be protected by a surfactant.

The surfactant in this embodiment is not particularly limited and may be any surfactant as long as it can form a particle. For example, a nonionic surfactant, an anionic surfactant, a cationic surfactant, a polymeric surfactant, or a phospholipid may be used. One kind of those surfactants may be used alone, or two or more kinds thereof may be used in combination.

Examples of the nonionic surfactant may include: polyoxyethylene sorbitan-based fatty acid esters such as Tween (trademark) 20, Tween (trademark) 40, Tween (trademark) 60, Tween (trademark) 80, and Tween (trademark) 85; and Brij (trademark) 35, Brij (trademark) 58, Brij (trademark) 76, Brij (trademark) 98, Triton (trademark) X-100, Triton (trademark) X-114, Triton (trademark) X-305, Triton (trademark) N-101, Nonidet (trademark) P-40, IGEPAL (trademark) CO530, IGEPAL (trademark) CO630, IGEPAL (trademark) CO720, and IGEPAL (trademark) CO730.

Examples of the anionic surfactant may include: sodium dodecyl sulfate; and a dodecylbenzenesulfonate, a decylbenzenesulfonate, an undecylbenzenesulfonate, a tridecylbenzenesulfonate, and a nonylbenzenesulfonate, and sodium, potassium, and ammonium salts thereof.

Examples of the cationic surfactant may include cetyltrimethylammonium bromide, hexadecylpyridinium chloride, dodecyltrimethylammonium chloride, and hexadecyltrimethylammonium chloride.

Examples of the polymeric surfactant may include polyvinyl alcohol, polyoxyethylene polyoxypropylene glycol, and gelatin. As a commercially available product of polyoxyethylene polyoxypropylene glycol, for example, Pluronic F68 (manufactured by BASF) and Pluronic F127 (manufactured by BASF) are given.

Examples of the phospholipid may include a phosphatidyl-based phospholipid having any one of the functional groups, i.e., an amino group, an NHS group, a maleimide group, and a methoxy group, and a PEG chain.

Examples of the phosphatidyl-based phospholipid may include 3-(N-succinimidyloxyglutaryl) aminopropyl, polyethyleneglycol-carbamyl distearoylphosphatidyl-ethanolamine (DSPE-PEG-NHS), N-(3-maleimide-1-oxopropyl) aminopropyl polyethyleneglycol-carbamyl distearoylphosphatidyl-ethanolamine (DSPE-PEG-MAL), N-(aminopropyl polyethyleneglycol)-carbamyl distearoylphosphatidyl-ethanolamine (DSPE-PEG-NH2), N-(carbonyl-methoxypolyethyleneglycol 2000)-1,2-distearoyl-sn-glycero-3-phosphoethanolamine, sodium salt (SUNBRIGHT DSPE-020CN), and N-(carbonyl-methoxypolyethyleneglycol 5000)-1,2-distearoyl-sn-glycero-3-phosphoethanolamine, sodium salt (SUNBRIGHT DSPE-050CN).

(Production Method for Particle)

A known method can be utilized as a production method for the particle of the present invention. Examples thereof may include a nanoemulsion method and a nanoprecipitation method.

As a solvent to be used in this production method, there may be given: hydrocarbons such as hexane, cyclohexane, and heptane; ketones such as acetone and methyl ethyl ketone; ethers such as diethyl ether and tetrahydrofuran; halogenated hydrocarbons such as dichloromethane, chloroform, carbon tetrachloride, dichloroethane, and trichloroethane; aromatic hydrocarbons such as benzene and toluene; esters such as ethyl acetate and butyl acetate; aprotic polar solvents such as N,N-dimethylformamide and dimethylsulfoxide; and pyridine derivatives. Those solvents may be used alone or may be arbitrarily mixed before use.

In the nanoemulsion method, an emulsion may be prepared by a conventionally known emulsifying technique. Examples of the conventionally known method include an intermittent shaking method, a stirring method utilizing a mixer such as a propeller type stirrer or a turbine type stirrer, a colloid mill method, a homogenizer method, and an ultrasonic irradiation method. Those methods may be used alone or in combination. Further, an emulsion may be prepared by one-step emulsification or may be prepared by multi-step emulsification. In this regard, however, the emulsifying technique is not limited to the above-mentioned techniques in such a range that the object of the present invention can be achieved.

In the nanoprecipitation method, a particle may be prepared by conventionally known methods involving: mixing an organic solvent dispersion into a surfactant-dispersed aqueous solution; and stirring the mixture, or a method involving: mixing a surfactant-dispersed aqueous solution into an organic solvent dispersion; and stirring the mixture.

(Organic Solvent Dispersion Having Material Containing Hydrophobic Dye Having Cyanine Structure Dissolved Therein)

A weight ratio between the surfactant-dispersed aqueous solution and organic solvent dispersion to be used in the nanoemulsion method is not particularly limited as long as an oil-in-water (O/W) type emulsion can be formed. The weight ratio between the organic solvent dispersion and the aqueous solution may fall within the range of 1:2 to 1:1,000.

A weight ratio between the surfactant-dispersed aqueous solution and organic solvent dispersion to be used in the nanoprecipitation method is not particularly limited as long as a particle can be collected. The weight ratio between the organic solvent dispersion and the aqueous solution may fall within the range of 1:1 to 1:1,000.

(Distillation of Organic Solvent from Particle Dispersion)

Distillation may be carried out by any conventionally known method, and examples thereof may include a method involving removal by heating and a method utilizing a pressure reducing device such as an evaporator.

In the nanoemulsion method, a heating temperature in the case of the removal by heating is not particularly limited as long as an O/W type emulsion can be maintained. However, the temperature may fall within the range of 0° C. to 80° C.

In the nanoprecipitation method, a heating temperature in the case of the removal by heating is not particularly limited as long as higher order aggregation, which reduces the yield of a particle, can be prevented. However, the temperature may fall within the range of 0° C. to 80° C.

In this regard, however, the distillation is not limited to the above-mentioned techniques in such a range that the object of the present invention can be achieved.

(Purification of Particle Dispersion)

The purification of a produced particle dispersion may be carried out by any conventionally known method. Examples thereof may include a size exclusion column chromatography method, an ultrafiltration method, a dialysis method, and a centrifugation method.

In this regard, however, the purification method is not limited to the above-mentioned techniques in such a range that the object of the present invention can be achieved.

(Particle)

A particle according to this embodiment may have any shape as long as the particle contains the above-mentioned hydrophobic dye having a cyanine structure, and examples of the shape include a spherical shape, an elliptical shape, a planar shape, and a one-dimensional string shape. The size (particle size) of the particle according to this embodiment is not particularly limited but is preferably 1 nm or more and 200 nm or less.

(Contrast Agent)

A contrast agent according to this embodiment contains the above-mentioned particle according to this embodiment and a dispersion medium. The dispersion medium is a liquid substance, and examples thereof include saline, distilled water for injection, and phosphate buffered saline (hereinafter may be abbreviated as PBS). Further, the contrast agent according to this embodiment may contain a pharmacologically acceptable additive as necessary.

In the contrast agent according to this embodiment, the above-mentioned particle may be dispersed in advance in a dispersion medium, or a kit including the particle according to this embodiment and a dispersion medium may be prepared and the particle may be used by being dispersed in the dispersion medium before administered to the body.

The particle according to this embodiment hardly causes the leakage of a hydrophobic dye and hence it can contain a large amount of the hydrophobic dye in itself. As the content of the dye increases, the amount of light absorption increases. Hence, the particle according to this embodiment is suitable for a photoacoustic imaging application or a fluorescence imaging application as described later. It should be noted that, when the content of the hydrophobic dye is so high as to cause concentration quenching, the particle according to this embodiment is more suitable for a photoacoustic imaging application.

(Photoacoustic Imaging Method)

The contrast agent according to this embodiment may be used for a photoacoustic imaging method. It should be noted that the term "photoacoustic imaging" as used herein is a concept including photoacoustic tomography (tomogram method). A photoacoustic imaging method using the contrast agent according to this embodiment is characterized by including at least the steps of: administering the contrast agent according to this embodiment to a specimen or a sample obtained from the specimen; irradiating the specimen or the sample obtained from the specimen with pulse light; and measuring a photoacoustic signal from a substance derived from the particle present in the specimen or in the sample obtained from the specimen.

An example of the photoacoustic imaging method using the contrast agent according to this embodiment is as described below. That is, the contrast agent according to this embodiment is administered to a specimen, or it is added to a sample such as an organ obtained from the specimen. It should be noted that the specimen refers to all living organisms such as a human being, an experimental animal, and a pet without any particular limitation. Examples of the specimen or the sample obtained from the specimen may include an organ, a tissue, a tissue section, a cell, and a cell lysate. After the administration or addition of the particle, the specimen or the like is irradiated with laser pulse light having a wavelength in a near infrared region.

In the photoacoustic imaging method according to this embodiment, the wavelength of irradiation light may be selected depending on a laser light source to be used. In the photoacoustic imaging method according to this embodiment, in order to efficiently acquire an acoustic signal, light having a wavelength of 600 nm to 1,300 nm in a near infrared region called "the biological window", where the influence of absorption and diffusion of light in the body is small, may be used.

A photoacoustic signal (acoustic wave) from the contrast agent according to this embodiment is detected and converted to an electrical signal with an acoustic wave detector such as a piezoelectric transducer. Based on the electrical signal obtained with the acoustic wave detector, the position or size of an absorber in the specimen or the like, or the optical characteristic value distribution of a molar absorption coefficient or the like, can be calculated. For example, when the contrast agent is detected above a threshold as a reference, a substance derived from the particle is estimated to be present in the specimen, or a substance derived from the particle can be estimated to be present in the sample obtained from the specimen.

In the present invention, quenching through the accumulation of the dye is caused by suppressing the leakage of a dye, and thus the energy of irradiation pulse light can be prevented from being used for fluorescent emission and it can be converted to higher thermal energy. Therefore, an acoustic signal can be acquired more efficiently.

(Fluorescence Imaging Method)

The contrast agent according to this embodiment may also be used for a fluorescence imaging method. A fluorescence imaging method using the contrast agent according to this embodiment is characterized by including at least the steps of: administering the contrast agent according to this embodiment to a specimen or a sample obtained from the specimen; irradiating the specimen or the sample obtained from the specimen with light; and measuring fluorescence from a substance derived from the particle present in the specimen or in the sample obtained from the specimen.

An example of the fluorescence imaging method using the contrast agent according to this embodiment is as described below. That is, the contrast agent according to this embodiment is administered to a specimen, or is added to a sample such as an organ obtained from the specimen. It should be noted that the specimen refers to all living organisms such as a human being, an experimental animal, and a pet without any particular limitation. Examples of the specimen or the sample from the specimen may include an organ, a tissue, a tissue section, a cell, and a cell lysate. After the administration or addition of the particle, the specimen or the like is irradiated with light having a wavelength in a near infrared region.

In the photoacoustic imaging method according to this embodiment, the wavelength of irradiation light may be selected depending on a laser light source to be used. In the fluorescence imaging method according to this embodiment, in order to efficiently acquire an acoustic signal, light having a wavelength of 600 nm to 1,300 nm in a near infrared region called "the biological window", where the influence of absorption and diffusion of light in the body is small, may be used.

Fluorescence from the contrast agent according to this embodiment is detected and converted to an electrical signal with a fluorescence detector. Based on the electrical signal obtained with the fluorescence detector, the position or size of an absorber in the specimen or the like can be calculated. For example, when the contrast agent is detected above a threshold as a reference, a substance derived from the particle is estimated to be present in the specimen, or a substance derived from the particle can be estimated to be present in the sample obtained from the specimen.

Hereinafter, each of the embodiments is described.

<First Embodiment>

(Construction of First Embodiment)

Figure 1:
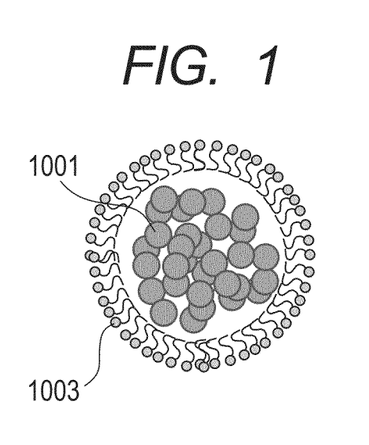
FIG. 1 is a view for illustrating a particle according to a first embodiment of the present invention.

As illustrated in FIG. 1, the particle according to this embodiment contains a hydrophobic dye 1001 having a cyanine structure and it contains a surfactant 1003 on its particle surface, in which the hydrophobic dye is represented by the chemical formula (1).

As described above, the hydrophobic dye having a cyanine structure according to this embodiment has a structure having high hydrophobicity while it has no (or even so, a reduced number of) hydrophilic functional group. Hence it hardly leaks out of the particle even in an aqueous solution such as serum. Further, a hydrophobic interaction between the molecules of the dye is considered to occur. Therefore, the dye hardly leaks out of the particle in serum.

(Concentration of Material in Organic Solvent Dispersion Having Material Containing Hydrophobic Dye Having Cyanine Structure Dissolved Therein)

The concentration of the hydrophobic dye having a cyanine structure in an organic solvent dispersion is not particularly limited as far as it is dissolved. The concentration of the hydrophobic dye having a cyanine structure may be set to 0.0005 to 300 mg/ml.

<Second Embodiment>

(Construction of Second Embodiment)

Figure 2:
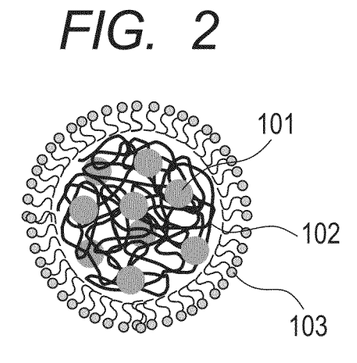
FIG. 2 is a view for illustrating a particle according to a second embodiment of the present invention.

As illustrated in FIG. 2, the particle according to this embodiment contains a hydrophobic dye 101 having a cyanine structure and a matrix material 102 encapsulating the hydrophobic dye, characterized in that the hydrophobic dye is represented by the chemical formula (1). It should be noted that the particle may contain a surfactant 103 on its surface.

As described above, the hydrophobic dye having a cyanine structure according to this embodiment has a structure having high hydrophobicity while it has no (or even so, a reduced number of) hydrophilic functional group. Hence it hardly leaks out of the particle even in an aqueous solution such as serum. Further, when a hydrophobic polymer such as poly (lactide-co-glycolide) acid (hereinafter may be abbreviated as PLGA) is used as the matrix material, a hydrophobic interaction between the PLGA and dye is considered to occur. Consequently, the dye alone hardly leaks out of the particle in serum.

Further, the dye and the hydrophobic matrix material are dissolved with each other and homogeneously dispersed, which results in an increase in light absorption amount per dye and an increase in photoacoustic signal intensity per dye.

(Matrix Material)

The matrix material may be any material as long as it can encapsulate the hydrophobic dye having a cyanine structure. Since a hydrophobic interaction with the hydrophobic dye increases and thus the leakage of the dye can be prevented more efficiently, a hydrophobic polymer may be used.

(Hydrophobic Polymer)

Examples of the hydrophobic polymer in this embodiment include a homopolymer formed of a monomer having a hydroxycarboxylic acid and having 6 or less carbon atoms, and a copolymer formed of two or more kinds of the monomer.

Considering when the contrast agent according to this embodiment is administered into the body, in order to prevent the contrast agent from remaining in the body over a long period of time, a polymer formed of a monomer having a hydroxycarboxylic acid and having 6 or less carbon atoms may be used as the hydrophobic polymer. This is because the polymer formed of a monomer having a hydroxycarboxylic acid and having 6 or less carbon atoms has an ester bond to be cleaved by a biological enzyme. Since a polymer having a cleaved ester bond is easily metabolized, it hardly remains in the body.

Examples of the polymer formed of a monomer having a hydroxycarboxylic acid and having 6 or less carbon atoms include polylactic acid (PLA), polyglycolic acid (PGA), and poly(lactide-co-glycolide) acid (PLGA).

The hydrophobic polymer may have a hydrophilic moiety. Examples of such polymer include polymethyl methacrylate, polyethyl methacrylate, polybutyl methacrylate, and polyisobutyl methacrylate.

The weight average molecular weight of the hydrophobic polymer is preferably 2,000 to 1,000,000, more preferably 10,000 to 600,000.

PLGA is particularly used as the matrix material in the particle according to this embodiment. Since PLGA has high hydrolyzability, it is expected to exhibit effects of being hardly accumulated in the body and being eliminated out of the body when it becomes unnecessary. A composition ratio between lactic acid and glycolic acid in the PLGA is not particularly limited, and PLGA having any composition ratio may be used. Examples thereof may include PLGAs having composition ratios between lactic acid and glycolic acid of 25:75, 50:50, and 75:25. Any of D-lactic acid, L-lactic acid, and a mixture thereof including racemic lactic acid may be used as lactic acid constituting the PLGA.

(Concentration of Material in Organic Solvent Dispersion Having Material Containing Hydrophobic Dye Having Cyanine Structure Dissolved Therein)

The concentrations of the polymer and the hydrophobic dye having a cyanine structure in an organic solvent dispersion are not particularly limited as far as they are dissolved. The concentration of the polymer may be set to 0.3 to 100 mg/ml. Further, the concentration of the hydrophobic dye having a cyanine structure may be set to 0.0005 to 300 mg/ml.

Further, a weight ratio between the hydrophobic dye having a cyanine structure and the polymer in the organic solvent dispersion may fall within the range of 100:1 to 1:1,000.

EXAMPLES

Hereinafter, the present invention is described by way of examples in order to further clarify the features of the present invention. However, the present invention is by no means limited to these examples. Materials, composition conditions, reaction conditions, and the like can be freely modified in such a range that a contrast agent having a similar function and effect can be expected.

(Collection Method)

A centrifugation operation was performed through use of a high speed refrigerated micro centrifuge (manufactured by TOMY SEIKO CO., LTD., MX-300). An ultracentrifugation operation was performed through use of a micro ultracentrifuge (manufactured by Hitachi Koki Co., Ltd., CS150GXL).

(Analysis Method)

The measurement of a particle size was performed through use of a dynamic light scattering analyzer (manufactured by Otsuka Electronics Co., Ltd., ELSZ-2).

The measurement was performed through use of semiconductor laser as a light source, and a value for a cumulant size was adopted as the particle size.

The measurement of a light absorbance was performed through use of a UV-VIS-NIR spectrophotometer (manufactured by PerkinElmer Inc., Lambda Bio 40).

(Evaluation Method for Photoacoustic Characteristics)

The measurement of a photoacoustic signal involves: irradiating a sample with pulse laser light; detecting a photoacoustic signal from the sample through use of a piezoelectric element; and amplifying the signal with a high speed preamplifier, followed by acquisition with a digital oscilloscope. Specific conditions for the measurement are as described below. Titanium sapphire laser (manufactured by Lotis Ltd.) was used as a light source. The conditions of a wavelength of 790 nm, an energy density of 12 mJ/cm$^2$, a pulse width of 20 nanoseconds, and a pulse repetition of 10 Hz were employed. Model V303 (manufactured by Panametrics-NDT) was used as an ultrasonic transducer. The conditions of a central frequency of 1 MHz, an element size of $\phi$0.5, a measurement distance of 25 mm (non-focus), and an amplification of +30 dB (Ultrasonic Preamplifier Model 5682 manufactured by Olympus Corporation) were employed. A measurement vessel was a cuvette made of polystyrene and having an optical path length of 0.1 cm and a sample volume of about 200 µl. DPO4104 (manufactured by TEKTRONIX, INC.) was used as a measuring device, and measurement was performed under the conditions of: trigger: detection of photoacoustic light with a photodiode; and data acquisition: 128 times (128 pulses) in average.

(Calculation Method for Molar Absorption Coefficient Per Particle)

The weight concentration of a solid component in a particle dispersion was calculated by freeze-drying the dispersion . . . . (A)

On the assumption that the density of each constituent material was 1 (g/cm$^3$), a weight per particle was calculated from the particle size of each particle . . . . (B)

The particle concentration of the particle dispersion was calculated by dividing the weight concentration determined in (A) by the weight per particle determined in (B) . . . . (C)

Based on the result of the light absorbance measurement and the result of (C), a molar absorption coefficient per particle was calculated.

(Evaluation of Dye-Holding Ability of Particle in Fetal Bovine Serum (FBS))

In order to compare the dye-holding abilities of produced particles, an evaluation was performed through use of FBS (manufactured by Life Technologies Corporation). 200 µL of a sample were dispersed in 1,800 µL of FBS and left to stand still at 36° C.

One day later, the dispersion was subjected to ultracentrifugation at 288,000 G. Thus, a supernatant was collected. The light absorbances of the dispersion and the supernatant were measured.

The ratio of a dye remaining in a particle was calculated based on the following equation.

Ratio of dye remaining in particle=(1−Light absorbance of supernatant/Light absorbance of dispersion)×100

(Calculation Method for Effective Molar Absorption Coefficient Per Particle)

The amounts of dyes remaining in particles in FBS as effective molar absorption coefficients were used for comparison.

An effective molar absorption coefficient per particle was calculated based on the following equation.

Effective molar absorption coefficient per particle=Molar absorption coefficient per particle×Ratio of dye remaining in particle (Evaluation Method for Hydrophobicity Degree of Hydrophobic Dye Having Cyanine Structure)

In order to compare the hydrophobicity degrees of hydrophobic dyes each having a cyanine structure, an evaluation was performed through use of a thin-layer liquid chromatography (hereinafter may be abbreviated as TLC) method.

A TLC glass plate RP-18 (manufactured by Merck) was used as a plate for development, and a methanol solution containing 1 wt % of lithium chloride was used as a developing solvent.

According to an ordinary method, a dye solution was spotted on the origin, and a relative migration distance (hereinafter may be abbreviated as Rf value) was calculated based on the following equation.

Rf value=Distance from origin to center of spot of component/Distance from origin to solvent front (Calculation Methods for Molar Absorption Coefficient Per Particle in Terms of 100 nm, Effective Molar Absorption Coefficient Per Particle in Terms of 100 nm, and Photoacoustic Signal Per Particle in Terms of 100 nm)

A molar absorption coefficient per particle, an effective molar absorption coefficient, and a photoacoustic signal per particle were each calculated through use of actual particle size data. After that, calculation was performed on the assumption that each of the values was proportional to a volume ratio when a 100-nm particle having the same composition was present.

(Blood Concentration Determination Experiment Using Particle)

Female outbred BALB/c Slc-nu/nu mice (six-week-old at the time of purchase) (Japan SLC, Inc.) were used. For 1 week before administration to the mice, the mice were habituated through use of a normal diet and bed under such an environment that the diet and drinking water were available ad libitum. 0.2 mL of a particle solution was intravenously injected to the habituated mice.

The cancer-bearing mice to which the particle solution was administered did not show any visual problem after the administration, and the whole injection was found to be well tolerated.

The blood was collected 1 hour and 24 hours after the administration. The collected blood was transferred to a plastic tube, and a 1% Triton-X100 aqueous solution was added in a 4.5-fold volume with respect to the volume of the blood. Next, dimethyl sulfoxide was added in a 4.5-fold volume with respect to the volume of the blood. Thus, a blood lysate was produced. The fluorescence intensity of the blood lysate in the plastic tube was measured through use of IVIS (trademark) Imaging System 200 Series (XENOGEN).

Further, a particle solution having a known concentration was diluted with a 1% Triton-X100 aqueous solution so as to achieve various concentrations. Each of the diluted particle solutions was mixed with an equal amount of blood collected from untreated mice. Next, a 1% Triton-X100 aqueous solution was added so that the total volume of the aqueous solution and the diluted particle solution was a 4.5-fold volume with respect to the volume of the blood. Next, dimethyl sulfoxide was added in a 4.5-fold volume with respect to the volume of the blood. Thus, a blood particle solution for a calibration curve was produced. In the same manner as in the collected blood sample, a fluorescence intensity was measured, and a calibration curve was prepared.

Next, the fluorescence intensity of the blood lysate and the prepared calibration curve were used to calculate a blood concentration.

A ratio of abundance in blood per dose (% ID) was calculated by dividing each of the calculated blood concentrations by the total dose.

Example 1

3.1 mg of 1,1',3,3,3',3'-hexamethylindotricarbocyanine iodide <chemical formula (A1)> (manufactured by Sigma-Aldrich Co. LLC.) as a dye were dissolved in 1.6 mL of chloroform.

20 mg of PLGA (manufactured by Wako Pure Chemical Industries, Ltd.) as a matrix material were added thereto. Thus, an organic solvent dispersion was prepared.

60 mg of Tween 20 (manufactured by Tokyo Chemical Industry Co., Ltd.) as a surfactant and 7.3 mg of SUN-BRIGHT DSPE-020CN (manufactured by NOF CORPORATION) were added to 20 mL of ultrapure water. Thus, a surfactant-dispersed aqueous solution was prepared.

To the stirred surfactant-dispersed aqueous solution, the organic solvent dispersion was added dropwise. Thus, a pre-emulsion liquid was prepared.

The pre-emulsion liquid was subjected to ultrasonic irradiation through use of an ultrasonic disperser (manufactured by TOMY SEIKO CO., LTD., UD-200) at an intensity scale of 4 for 1 minute and 30 seconds. Thus, an emulsion was produced.

In order to remove chloroform from the emulsion, heating stirring was performed at 40° C. for 2 hours. Thus, a particle dispersion was produced.

The resultant particle dispersion was dialyzed with a dialysis membrane having a molecular weight cut-off of 300,000 to remove an excess amount of the surfactant or the like.

The collected particle dispersion was filtered through a filter having a pore diameter of 0.20 micrometer. Thus, a particle (A-1) was obtained.

Example 2

A particle (A-2) was obtained by the same synthesis procedures as those of Example 1 except that the dye was changed to 3H-indolium, 1-ethyl-2-[7-(1-ethyl-1,3-dihydro-3,3-dimethyl-2H-indol-2-ylidene)-1,3,5-heptatrien-1-yl]-3,3-dimethyl-, iodide <chemical formula (A2)> (manufactured by Hayashibara Co., Ltd., hereinafter the same compound obtained from the same).

Example 3

A particle (A-3) was obtained by the same synthesis procedures as those of Example 1 except that the dye was changed to 2-[2-[2-chloro-3-[2-(1,3-dihydro-1,1,3-trimethyl-2H-benzo[e]-indol-2-ylidene)-ethylidene]-1-cyclohexen-1-yl]-ethenyl]-1,1,3-trimethyl-1H-benzo[e]indolium perchlorate <chemical formula (A3)> (manufactured by Sigma-Aldrich Co. LLC.).

Example C-1

3.1 mg of 1,1',3,3,3',3'-hexamethylindotricarbocyanine iodide <chemical formula (A1)> (manufactured by Sigma-Aldrich Co. LLC.) as a dye were dissolved in 1.6 mL of chloroform. Thus, an organic solvent dispersion was prepared.

180 mg of Tween 20 (manufactured by Wako Pure Chemical Industries, Ltd.) as a surfactant were added to 20 mL of ultrapure water. Thus, a surfactant-dispersed aqueous solution was prepared.

To the stirred surfactant-dispersed aqueous solution, the organic solvent dispersion was added dropwise. Thus, a pre-emulsion liquid was prepared.

The pre-emulsion liquid was subjected to ultrasonic irradiation through use of an ultrasonic disperser (manufactured by TOMY SEIKO CO., LTD., UD-200) at an intensity scale of 4 for 1 minute and 30 seconds. Thus, an emulsion was produced.

In order to remove chloroform from the emulsion, heating stirring was performed at 40° C. for 2 hours. Thus, a particle dispersion was produced.

The collected particle dispersion was filtered through a filter having a pore diameter of 0.20 micrometer. Thus, a particle (C-1) was obtained.

Example C-2

A particle (C-2) was obtained by the same synthesis procedures as those of Example C-1 except that the dye was changed to 1,1',3,3,3',3'-hexamethylindotricarbocyanine perchlorate <chemical formula (C1)> (manufactured by Sigma-Aldrich Co. LCC.).

Example C-3

A particle (C-3) was obtained by the same synthesis procedures as those of Example C-1 except that the dye was changed to 1,1',3,3,3',3'-hexamethyl-4,4',5,5'-dibenzo-2,2'-indotricarbocyanine perchlorate <chemical formula (C2)> (manufactured by Hayashibara Co., Ltd., hereinafter the same compound obtained from the same).

Example C-4

10.0 mg of 1,1',3,3,3',3'-hexamethylindotricarbocyanine iodide <chemical formula (A1)> (manufactured by Sigma-Aldrich Co. LLC.) as a dye were dissolved in 0.05 mL of dimethyl sulfoxide. Thus, an organic solvent dispersion was prepared.

0.45 mg of Tween 20 (manufactured by Wako Pure Chemical Industries, Ltd.) as a surfactant were added to 5.0 mL of ultrapure water. Thus, a surfactant-dispersed aqueous solution was prepared.

To the stirred surfactant-dispersed aqueous solution, the organic solvent dispersion was added dropwise. Thus, a particle dispersion was prepared.

The resultant particle dispersion was collected by centrifugation at 4° C. and 20,000 G for 45 minutes.

The collected particle was washed with ultrapure water. After that, the particle dispersion was collected by centrifugal separation at 4° C. and 20,000 G for 45 minutes.

The collected particle dispersion was filtered through a filter having a pore diameter of 1.2 μm. Thus, a particle (C-4) was obtained.

Example C-5

A particle (C-5) was obtained by the same synthesis procedures as those of Example C-4 except that the dye was changed to 3H-indolium, 1-ethyl-2-[7-(1-ethyl-1,3-dihydro-3,3-dimethyl-2H-indol-2-ylidene)-1,3,5-heptatrien-1-yl]-3,3-dimethyl-, iodide <chemical formula (A2)>.

Example C-6

A particle (C-6) was obtained by the same synthesis procedures as those of Example C-4 except that the dye was changed to 1,1',3,3,3',3'-hexamethyl-4,4',5,5'-dibenzo-2,2'-indotricarbocyanine perchlorate <chemical formula (C2)> (manufactured by).

Example C-7

A particle (C-7) was obtained by the same synthesis procedures as those of Example C-4 except that the dye was changed to 2-[2-[2-chloro-3-[2-(1,3-dihydro-1,1,3-trimethyl-2H-benzo[e]-indol-2-ylidene)-ethylidene]-1-cyclohexen-1-yl]-ethenyl]-1,1,3-trimethyl-1H-benzo[e]indolium perchlorate <chemical formula (A3)> (manufactured by Sigma-Aldrich Co. LLC.).

Comparative Example 1

ICG (5.5 mg, manufactured by Pharmaceutical and Medical Device Regulatory Science Society of Japan) was dissolved in 1 ml of methanol. Thus, an ICG methanol solution was prepared. DSPC (11.3 mg, manufactured by NOF CORPORATION) was dissolved in 2 ml of chloroform. Thus, a DSPC chloroform solution was prepared. 1 ml of the ICG methanol solution was mixed with 2 ml of the DSPC chloroform solution. After that, the solvent was distilled off under reduced pressure at 40° C. ICG and DSPC evaporated to dryness were dissolved in 2 ml of chloroform. Thus, an ICG composition containing ICG and DSPC dissolved in chloroform was prepared.

5 mg (molar ratio between lactic acid and glycolic acid=1:1, M.W.: 20,000, manufactured by Wako Pure Chemical Industries, Ltd.) of poly(lactide-co-glycolide) acid (PLGA) were dissolved in the ICG composition (1.6 ml). Thus, a chloroform solution was prepared.

Next, the chloroform solution was added to an aqueous solution (20 ml) having dissolved therein Tween 20 (180 mg, manufactured by Tokyo Chemical Industry Co., Ltd.) and N-(aminopropyl polyethyleneglycol)-carbamyl distearoylphosphatidyl-ethanolamine (5 mol %, 22 mg, DSPE-PEG-NH2, M.W. of PEG: 2,000, manufactured by NOF CORPORATION) to prepare a mixed liquid. The mixed liquid was stirred and then treated with an ultrasonic disperser for 90 seconds. Thus, an O/W type emulsion was prepared.

Next, the emulsion was subjected to reduced pressure treatment with a rotary evaporator (at 40° C. for 2 hours) to distill off chloroform from the dispersoid. Thus, a particle dispersion containing fine particles whose surfaces were protected by Tween 20 and the phospholipid, and containing ICG and DSPC in PLGA was produced.

The resultant particle dispersion was dialyzed with a dialysis membrane having a molecular weight cut-off of 300,000 to remove an excess amount of the surfactant or the like.

The collected particle dispersion was filtered through a filter having a pore diameter of 0.20 micrometer. Thus, a particle (A-4) was obtained.

Table 1 shows absorption maximum wavelengths, particle sizes, molar absorption coefficients per particle, photoacoustic signal intensities per particle (wavelength: 780 nm), and ratios of dyes remaining in particles in the particles (A-1) to (A-4) obtained in the foregoing. The molar absorption coefficients per particle and photoacoustic signal intensities per particle were compared in terms of a particle size assumed as 100 nm. The table also shows the evaluation results of hydrophobicity degrees (Rf values) of hydrophobic dyes used as dyes. Table 1 reveals that each of the particles (A-1) to (A-3) produced in this example had a higher ratio of a dye remaining in a particle and a higher effective molar absorption coefficient than those of the ICG-containing particle (A-4) according to Comparative Example.

Thus, each of the particles according to this example hardly causes the leakage of a dye and has a high molar absorption coefficient, and hence the particles are suitable for a contrast agent for fluorescence imaging or for photoacoustic imaging.

Reference Example 1

The molar absorption coefficient per particle predicted based on calculation of a particle containing a hydrophobic dye (IR26: chemical formula (7)) described in Nanomedicine. 2011 Apr. 7(2), 228-37 (Non Patent Literature 2) is shown in Table 1. It should be noted that there was no description of data on such a ratio of a dye remaining in a particle using FBS as described in the foregoing, and hence an effective molar absorption coefficient per particle was calculated on the assumption that 100% of a dye remained.

Chemical formula (7)

Reference Example 2

The molar absorption coefficient per particle predicted based on calculation of a particle containing a hydrophobic dye (DiR: chemical formula (8)) described in Proc. SPIE 7576, 75761H (2010) (Non Patent Literature 3) is shown in Table 1. It should be noted that there was no description of data on such a ratio of a dye remaining in a particle using FBS as described in the foregoing, and hence an effective molar absorption coefficient per particle was calculated on the assumption that 100% of a dye remained.

Chemical formula (8)

Table 1 reveals that each of the particles (A-1) to (A-3) produced in this example showed a higher effective molar absorption coefficient than the effective molar absorption coefficients per particle predicted from Non Patent Literature 2 and Non Patent Literature 3. It should be noted that since the particle containing IR26 shown in Reference Example 1 is prepared by a spray drying method, it had a large particle size. On the other hand, the particle in this example was prepared by a nanoemulsion method. Hence, a particle having a small particle size could be prepared and thus it is considered that a higher tumor accumulation property is exhibited when administered to the body.

TABLE 1

| Particle | Hydrophobic dye having cyanine structure | Rf value | Absorption maximum wavelength (nm) | Particle size (nm) | Molar absorption coefficient per particle in terms of 100 nm ($M^{-1}cm^{-1}$) | Ratio of dye remaining in particle (%) | Effective molar absorption coefficient per particle in terms of 100 nm ($M^{-1}cm^{-1}$) | Relative ratio of effective molar absorption coefficient per particle in terms of 100 nm | Photoacoustic signal per particle in terms of 100 nm ($VJ^{-1}M^{-1}$) |
|---|---|---|---|---|---|---|---|---|---|
| (A-1) | Chemical formula (A1) | 0.45 | 750 | 167 | 2.7E+09 | 44 | 1.2E+09 | 2.1 | 3.7E+10 |
| (A-2) | Chemical formula (A2) | 0.5 | 751 | 170 | 4.1E+09 | 24 | 9.9E+08 | 1.7 | 2.7E+10 |
| (A-3) | Chemical formula (A3) | 0.09 | 745 | 23 | 4.2E+10 | 19 | 7.2E+09 | 12 | 4.3E+11 |
| Chemical formula (A-4) | ICG | 0.78 | 791 | 83 | 4.8E+09 | 10 | 5.8E+08 | 1 | 8.6E+10 |
| Non Patent Literature 2 | IR26 | — | — | 486 | 5.6E+08 | 100 | 5.6E+08 | 1 | — |
| Non Patent Literature 3 | DiR | — | — | 50 | 3.2E+08 | 100 | 3.2E+08 | 0.6 | — |

Table C-1 shows absorption maximum wavelengths and particle sizes in the particles (C-1) to (C-3) obtained in the foregoing.

TABLE C-1

| Particle | Hydrophobic dye having cyanine structure | Rf value | Absorption maximum wavelength (nm) | Particle size (nm) |
|---|---|---|---|---|
| (C-1) | Chemical formula (A1) | 0.45 | 746 | 25 |
| (C-2) | Chemical formula (C1) | 0.45 | 746 | 19 |
| (C-3) | Chemical formula (C2) | 0.31 | 792 | 30 |

Table C-2 shows absorption maximum wavelengths, particle sizes, molar absorption coefficients per particle, photoacoustic signal intensities per particle (wavelength: 780 nm), and ratios of dyes remaining in particles in the particles (C-4) to (C-7) obtained in the foregoing. The molar absorption coefficients per particle and the photoacoustic signal intensities per particle were compared in terms of a particle size assumed as 100 nm.

Table C-2 reveals that each of the particles (C-4) to (C-7) produced in this example had a higher ratio of a dye in a particle and a higher effective molar absorption coefficient than those of the ICG-containing particle (A-4) according to Comparative Example.

TABLE C-2

| Particle | Hydrophobic dye having cyanine structure | Rf value | Absorption maximum wavelength (nm) | Particle size (nm) | Molar absorption coefficient per particle in terms of 100 nm ($M^{-1}cm^{-1}$) | Ratio of dye remaining in particle (%) | Effective molar absorption coefficient per particle in terms of 100 nm ($M^{-1}cm^{-1}$) | Relative ratio of effective molar absorption coefficient per particle in terms of 100 nm | Photoacoustic signal per particle in terms of 100 nm ($VJ^{-1}M^{-1}$) |
|---|---|---|---|---|---|---|---|---|---|
| (C-4) | Chemical formula (A1) | 0.45 | 737 | 173 | 3.4E+10 | 42 | 1.4E+10 | 25 | 2.0E+11 |
| (C-5) | Chemical formula (A2) | 0.5 | 739 | 185 | 5.6E+10 | 25 | 1.4E+09 | 2.4 | 1.5E+11 |
| (C-6) | Chemical formula (C2) | 0.31 | 708 | 119 | 2.3E+09 | 33 | 7.5E+08 | 1.3 | 8.2E+10 |
| (C-7) | Chemical formula (A3) | 0.09 | 741 | 108 | 1.9E+10 | 49 | 9.0E+09 | 16 | 9.7E+11 |
| (A-4) | ICG | 0.78 | 791 | 83 | 4.8E+09 | 10 | 5.8E+08 | 1 | 8.6E+10 |

Example F-1

Table F-1 shows the results of blood concentration determination experiments using particles for the particles (A-2) and (C-1) to (C-3) obtained in the foregoing.

The table also shows the results of a similar blood concentration determination experiment using ICG as Comparative Example F.

Table F-1 reveals that each of the particles (A-2) and (C-1) to (C-3) produced in this example had a higher ratio of abundance in blood per dose than that of the ICG of Comparative Example F.

Therefore, the particles produced in this example are each considered to exhibit high tumor accumulation property when administered to the body.

TABLE F-1

| Particle | Dye having cyanine structure | Ratio of abundance in blood per dose (% ID) |
|---|---|---|
| A-2 | Chemical formula (A2) | 39 |
| C-1 | Chemical formula (A1) | 5 |
| C-2 | Chemical formula (C1) | 5 |
| C-3 | Chemical formula (C2) | 4 |
| ICG (non-particle) | ICG | 1 |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-038035, filed Feb. 23, 2012, which is hereby incorporated by reference herein in its entirety.

What is claimed is:

1. A particle encapsulating a hydrophobic dye having a cyanine structure, the particle further comprising surfactants,
wherein the surfactants are a polyoxyethylene sorbitan-based fatty acid ester and a phospholipid,
wherein a size of the particle is from 1 nm to 200 nm, and
wherein the hydrophobic dye is selected from the group consisting of 1,1',3,3,3',3'-hexamethylindotricarbocyanine iodide (chemical formula (A1)); 3H-indolium, 1-ethyl-2-[7-(1-ethyl-1,3-dihydro-3,3-dimethyl-2H-indol-2-ylidene)-1,3,5-heptatrien-1-yl]-3,3-dimethyl-, iodide (chemical formula (A2)); 2-[2-[2-chloro-3-[2-(1,3-dihydro-1,1,3-trimethyl-2H-benzo[e]-indol-2-ylidene)-ethylidene]-1-cyclohexen-1-yl]-ethenyl]-1,1,3-trimethyl-1H-benzo[e]indoliumperchlorate (chemical formula (A3)); 1,1',3,3,3',3'-hexamethylindotricarbocyanine perchlorate (chemical formula (C1)); and 1,1',3,3,3',3'-hexamethyl-4,4',5,5'-dibenzo-2,2'-indotricarbocyanine perchlorate (chemical formula (C2)):

chemical formula (A1)

chemical formula (A2)

chemical formula (A3)

chemical formula (C1)

chemical formula (C2)

2. A contrast agent, comprising:
the particle according to claim 1; and
a dispersion medium.

3. The contrast agent according to claim 2, wherein the contrast agent is used for photoacoustic imaging.

4. The particle according to claim 1, wherein the polyoxyethylene sorbitan-based fatty acid ester is selected from the group consisting of polysorbate 20, polysorbate 40, polysorbate 60, polysorbate 80, and polysorbate 85.

5. The particle according to claim 1, wherein the polyoxyethylene sorbitan-based fatty acid ester is polysorbate 20.

6. The particle according to claim 1, wherein the hydrophobic dye is 1,1',3,3,3',3'-hexamethyl-4,4',5,5'-dibenzo-2,2'-indotricarbocyanine perchlorate (chemical formula (C2))

* * * * *